United States Patent [19]
Cloyd

[11] Patent Number: 5,166,889
[45] Date of Patent: Nov. 24, 1992

[54] ROBOTIC LIQUID SAMPLING SYSTEM

[75] Inventor: William C. Cloyd, Lexington, Ky.

[73] Assignee: Medical Robotics, Inc., Lexington, Ky.

[21] Appl. No.: 295,498

[22] Filed: Jan. 10, 1989

[51] Int. Cl.⁵ .............................................. G06F 15/20
[52] U.S. Cl. ...................................... 364/510; 211/77
[58] Field of Search .................... 364/510, 513; 141/1, 141/238, 130, 34; 211/77, 163

[56] References Cited

U.S. PATENT DOCUMENTS

| | | | |
|---|---|---|---|
| 3,863,507 | 2/1975 | Jones et al. | 141/130 |
| 3,932,131 | 1/1976 | Rolfo-Fontana | 141/130 |
| 4,041,994 | 8/1977 | Horwitz et al. | 141/1 |
| 4,058,252 | 11/1977 | Williams | 141/34 |
| 4,096,893 | 6/1978 | Harvey, Jr. et al. | 141/90 |
| 4,170,798 | 10/1979 | Krumdieck | 73/421 |
| 4,262,711 | 4/1981 | Anderson | 141/238 |
| 4,274,453 | 6/1981 | Lee | 141/1 |
| 4,342,341 | 8/1982 | Lee | 141/1 |
| 4,495,149 | 1/1985 | Iwata et al. | 141/130 |
| 4,835,711 | 5/1989 | Hutchins et al. | 364/513 |
| 4,849,177 | 7/1989 | Jordan | 211/77 |
| 4,956,148 | 9/1990 | Grandone | 211/77 |

*Primary Examiner*—Parshotam S. Lall
*Assistant Examiner*—Ellis B. Ramirez
*Attorney, Agent, or Firm*—Vance A. Smith

[57] ABSTRACT

A sampling system and method especially adapted for blood is provided wherein a plurality of sample tubes are positioned for ready access on a support wheel. The blood is processed by robotics under the control of a microprocessor that includes indexing of the wheel, identifying the container and indicating the condition of the blood. Signals indicating the index position of the wheel, fibrin or protein string in the serum of the blood, as well as other properties of the blood can be obtained in the processing system, the information maintained matched to the sample and analyzed, and data generated and stored without human intervention. To obtain the serum separation, the support wheel is placed in a centrifuge before the processing steps. The sample tubes are removably positioned between adjacent radial arms on the wheel and are pivotal in a pendulum fashion to allow the centrifuge operation. The wheel can be robotically picked up and moved to and from the centrifuge or storage positions. The tube holding unit includes a body and retainer for the tube and a laterally extending receiver for sample cups. A pendulum support bar includes magnetic detent means and an extension above the pivot pin for receipt in a recess in the body of the tube holding unit. The body of the unit also includes a concave reflector for photo energy scanning.

24 Claims, 2 Drawing Sheets

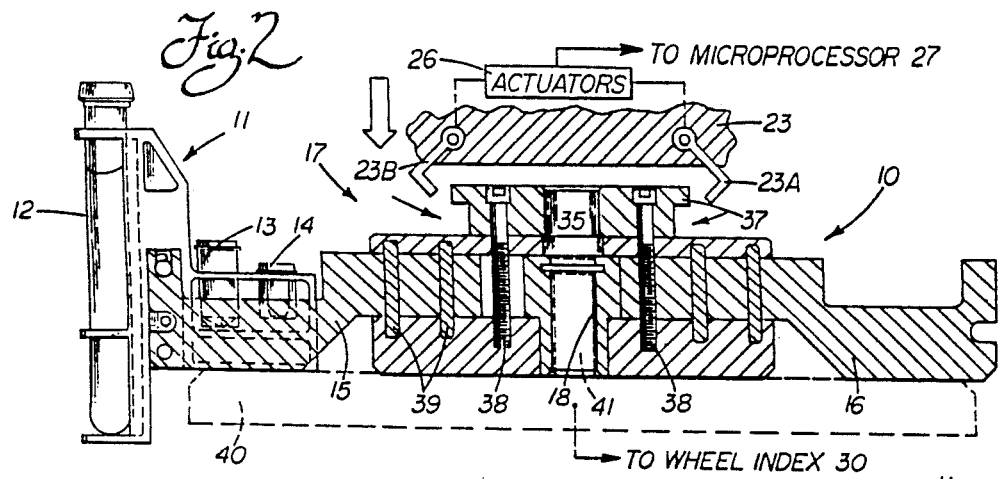
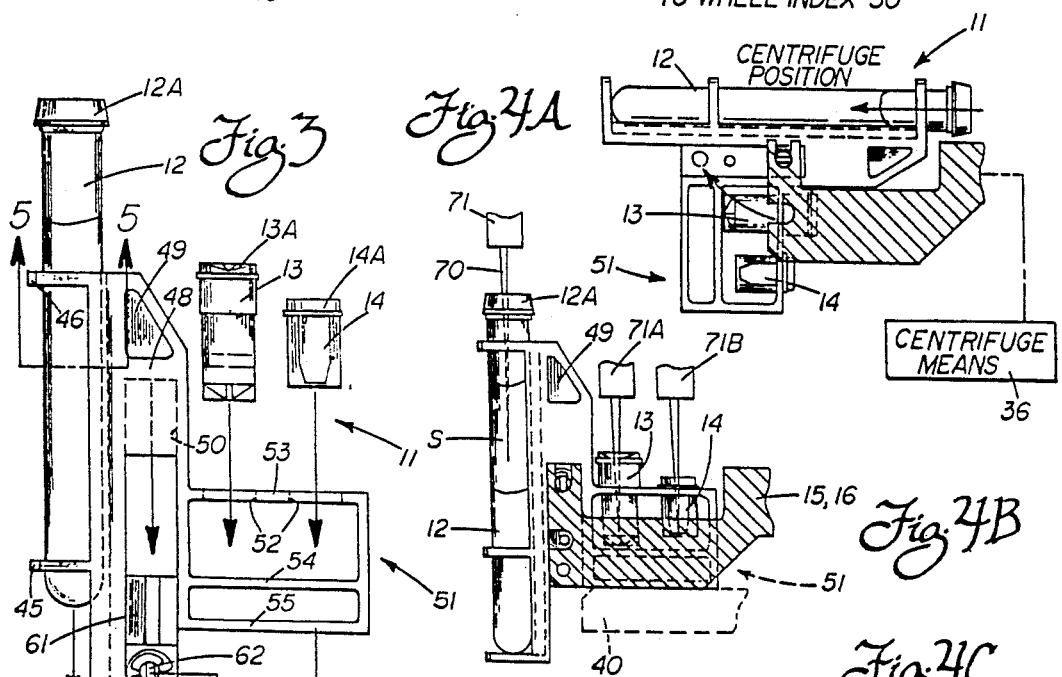
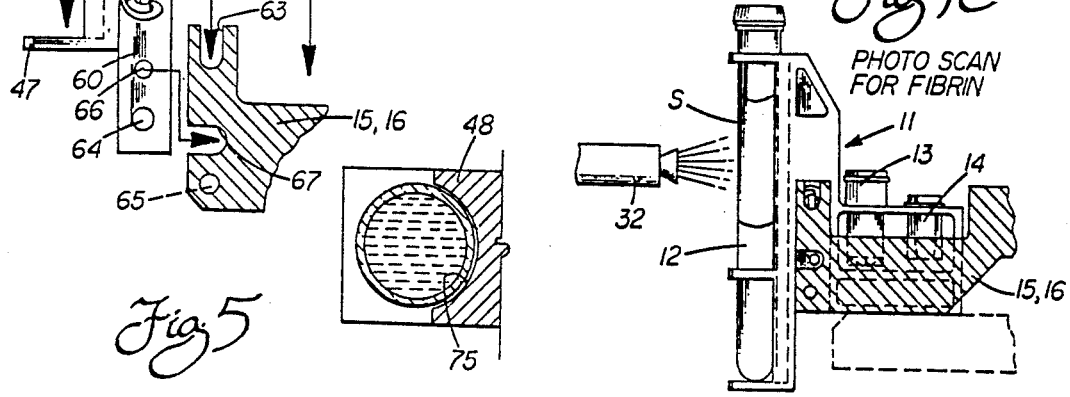

ROBOTIC LIQUID SAMPLING SYSTEM

BACKGROUND OF THE INVENTION

The present invention relates to liquid handling and analyzing, and more particularly, to an apparatus and method for processing blood samples including scanning and separating the samples without human intervention.

The modern clinical pathology lab of today includes several machines to accurately analyze blood samples for a wide range of characteristics and diseases. Recently, with the development of microprocessing equipment, more and more of the blood analysis can be quickly and accurately performed by automation. Electronic equipment capable of analyzing the condition of blood that was not even dreamed possible just a few years ago, such as analysis of cholesterol in the blood, is available on a wide scale. Other photo-analyzers for blood and its components have been developed and refined where they are now standard equipment in the laboratory. Analyzing techniques for viruses and other foreign bodies in the blood are rapidly advancing also.

While the analyzers per se have thus advanced rapidly in the past few years, the system for handling the blood samples in the sample tubes has remained substantially unchanged. The blood samples are generally taken by drawing directly from the patient into a pre-evacuated tube. A needle extending from the heavy rubber stopper of the tube is injected into a vein of the patient and the blood flows through the needle and into the tube due of ambient pressure. The sample tube is then manually labeled and transferred by a carrier to the centrifuge in another portion of the laboratory. At the centrifuge, the technician removes the sample tube from the carrier and places it into the centrifuge along with other samples (or sample tubes of water to balance the centrifuge).

The centrifuge is operative to separate the blood cells from the serum. This allows the pathologist and others to more efficiently study the blood sample. The standard practice is to remove the sample tube with the separated blood cells/serum and once again place the tube in another holder or rack whereupon the serum is aspirated from the upper portion of the tube. The aspiration step is usually performed manually. From this point, the sample tube along with the sample cups in which the serum has been placed must be tagged and are analyzed by machine, or visually by the pathologist or other technicians.

Throughout the process of manual handling of the sample tubes/cups, described above, the personnel are exposed to the potential of coming into contact with the blood. If a sample tube or cup breaks, the blood of the sample can inadvertently splash in the eyes or other cavity of the testing personnel. With the discovery of the AIDS virus, this contingency can even be deadly.

In addition to the risk involved in the manual handling of the blood, the cost of human intervention is substantial. Even more so today with the spreading of the AIDS virus, the personnel must be more highly trained and paid than before. The cost to the laboratory, and eventually to the general public, is becoming a major concern of the health industry.

Thus, a need is identified for a different approach to processing of blood samples, or broadly other dangerous liquids, where human intervention is minimized. The cost in paying humans to perform the handling/analyzing steps has simply become too great and the risk to human life is also not tolerable.

SUMMARY OF THE INVENTION

Accordingly, it is a primary object of the present invention to provide an apparatus and method of handling blood, or other hazardous liquids, while overcoming the above disadvantages and problems of the prior art.

It is another object of the present invention to provide a liquid sample processing system wherein the apparatus and the steps are performed by robotics controlled by a computer that is effective for analyzing and storing data indicative of the liquid condition.

It is still another object of the present invention to provide a processing system for liquids wherein a support for a plurality of sample tubes is provided in the form of a portable wheel that can serve as a bulk carrier for the tubes during centrifuging and processing, all by robotic control.

It is also an object of the present invention to provide an apparatus and related method wherein the samples within the tubes can be scanned, aspirated and transferred to sample cups, as well as other processing, without the need for exposure to humans.

It is a further object of the present invention to provide a wheel having support arms upon which tube holding units can be easily placed and by pendulum action allow centrifuging and at the same time analyzing without being removed from the wheel.

It is still a further object of the present invention to provide a tube holding unit for use with a support wheel or the like, wherein sample cups can be held adjacent the tube throughout the entire processing operation.

It is still a further object of the present invention to provide a tube holding unit for a sample tube and sample cups with a provision for mounting on a pendulum between the two.

Additional objects, advantages and other novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects, and in accordance with the purposes of the present invention as described herein, an improved apparatus and method is provided for processing liquids, such as blood, to determine the characteristic or composition thereof. The processing system includes a support means that holds a plurality of sample containers for easy access. An index means is provided for the support means so that selected container can be positioned at a sampling station upon command. A robotic processor at the sampling station is operative to process the liquid sample and corresponding signal generating means identifies the container and indicates the condition of the liquid being processed. A computer is provided for analyzing and storing data in response to the signals with the end result being that the liquid may be analyzed and data generated and stored without human intervention. Although the preferred embodiment will be described hereinafter as relating to blood, it should be realized by those skilled in the art that other hazardous sample liquids, such as radioactive liquids, can be advantageously processed by the system of the present invention.

the related method comprises the steps of supporting the containers for indexed access at a sampling station, indexing the containers to the sampling station, processing the sample, generating a signal to identify the container and the condition of the liquid, and analyzing/storing of the data from the signals generated. By practicing the method, the liquid, such as contaminated blood, may be analyzed and corresponding data generated and stored without human intervention, and, thus, without human risk.

The computer means of the system preferably includes a microprocessor, a keyboard or the like for programming the microprocessor and memory or data storage means. Scanners are provided to generate the signals and an indexing means, such as a stepping motor, can be used for the movement of the support means, as well as for all robotic actuators required for the system. A feedback is provided to provide the microprocessor with position information on a continuous basis.

Preferably, the containers comprise sample tubes and the tubes are supported on a wheel having a plurality of radial support arms. The tubes are held in holding units removably positioned between the adjacent arms. The central hub of the wheel has an annular shoulder that allows robotic transfer of the wheel to and from the centrifuge and/or other storage locations.

Each tube holding unit includes a body and retainer rings for the tube. In addition, in accordance with the present invention, each tube holding unit has a laterally extending receiver for sample cups. The sample cups are operative to receive a portion of the liquid from the sample tube. Due to the integral design of the holding unit, all of the component parts are advantageously kept together with the present invention. Preferably, there are two cups associated with each tube and the cups are positioned substantially parallel to the sample tube in the space between the adjacent arms of the wheel.

Each holding unit is supported by a pendulum support bar including a detent for retaining the holding unit in the upright position. Because of the pendulum or pivoting action, the tubes and sample cups can swing outwardly during the centrifuge operation utilizing the wheel. The pendulum bar is received in a recess between the sample tube and the sample cups. The detent is preferably a bar magnet on the pendulum support bar cooperating with disc magnets having opposite poles on the adjacent arms. An over travel pin may be provided on the support bar to cooperate with a recess on the support arms. A concave reflector is provided on the tube holding unit so that photo energy transmitted through the tube can be reflected back for scanning in an improved fashion.

The process means in accordance with the present invention includes a novel processing head that mounts at least one aspirator for robotically entering and removing at least a portion of the liquid from the container, such as the separated serum of centrifuged blood. The aspirator(s) are mounted on a robotically controlled telescoping portion, and enter and withdraw from the tube under robotic control.

A robotic arm is provided in accordance with the invention to pick up the wheel for transfer by means of opposed clamps. The clamps engage an annular shoulder on the hub. The wheel serves as a bulk storage unit so that the entire processing operation can be carried out at more than one position.

In order to identify the sample being processed at the sampling station, the distal ends of the arms may be provided with a code indicia that is read by the position scanner. The microprocessor is provided with the appropriate information and controls the robotic actuators under exact control.

Still other objects of the present invention will become readily apparent to those skilled in this art from the following description wherein there is shown and described a preferred embodiment of this invention, simply by way of illustration of one of the modes best suited to carry out the invention. As it will be realized, the invention is capable of other different embodiments, and its several details are capable of modifications in various, obvious aspects all without departing from the invention. Accordingly, the drawings and descriptions will be regarded as illustrative in nature and not as restrictive

BRIEF DESCRIPTION OF THE DRAWINGS

The accompanying drawings incorporated in and forming a part of the specification, illustrate several aspects of the present invention, and together with the description serve to explain the principles of the invention. In the drawings:

FIG. 2 is a cross-sectional view taken along a line adjacent the tube holding unit with the pick-up head for the support wheel being shown broken away and with the actuator illustrated schematically;

FIG. 3 is an exploded side view of the tube holding unit with the sample tube and sample cups illustrated to show their positioning and a cutaway portion of the distal end of the mounting support arm including the pendulum support bar;

FIG. 4A is a sectional view of the distal end of the support arm adjacent the tube holding unit showing the unit in the 90° pivoted mode during centrifuging;

FIG. 4B is a cross-sectional view taken along the distal end of the arm adjacent the tube holding unit showing the position of aspirators for the aspirating step of the procedure with the indexable turntable in position to support the holding unit;

FIG. 4C is a cross-sectional view of the distal end of the arm adjacent the holding unit similar to FIG. 4B but showing the scanning operation for locating the air/serum interface, fibrin or protein string and the serum/cell interface; and FIG. 5 is a cross-sectional view taken along line 5—5 of FIG. 3 and showing the concave reflector behind the tube.

Reference will now be made in detail to the present preferred embodiment of the invention, an example of which is illustrated in the accompanying drawings.

DETAILED DESCRIPTION OF THE INVENTION

Figure 1:
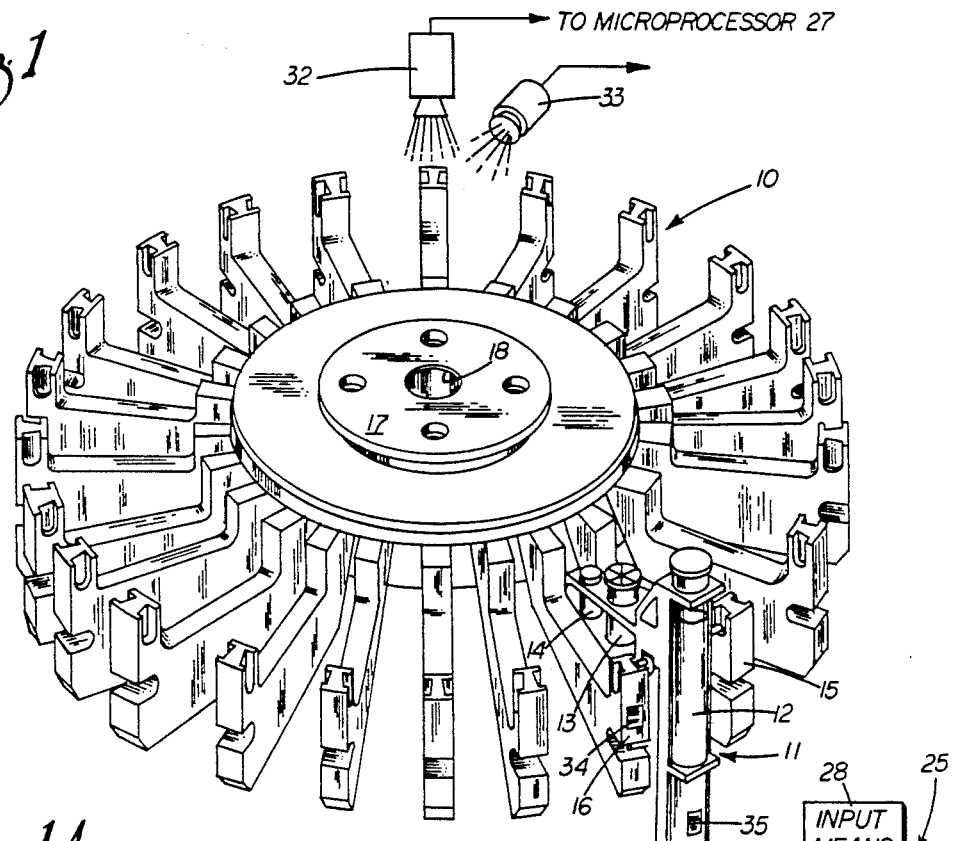
FIG. 1 is a perspective view of the support wheel of the sample processing system of the present invention, with all but one tube holding unit being removed for clarity of illustration.

With reference now to FIG. 1 of the drawings, a support wheel 10 is illustrated without being positioned in any associated equipment. An important aspect of the present invention is that the wheel 10 is portable and serves as a bulk storage device for a plurality of tube holding units 11 (only one shown in FIG. 1). The tube holding unit 11 will be described in greater detail below but at the along with one or two sample cups 13, 14 are positioned between adjacent radial support arms 15, 16 of the tube handling wheel 10. While in the preferred embodiment the sample tube 12 will be described as holding blood as the liquid, it is apparent that other dangerous liquids can be held and processed in accordance with the broader aspects of the present invention.

As also shown in FIG. 1, the radial arms 15, 16 are supported on a hub 17. A central aperture 18 is provided to receive the drive shaft of a centrifuge and the locating shaft of an indexible turntable, as will be apparent from the description below.

Figure 1A:
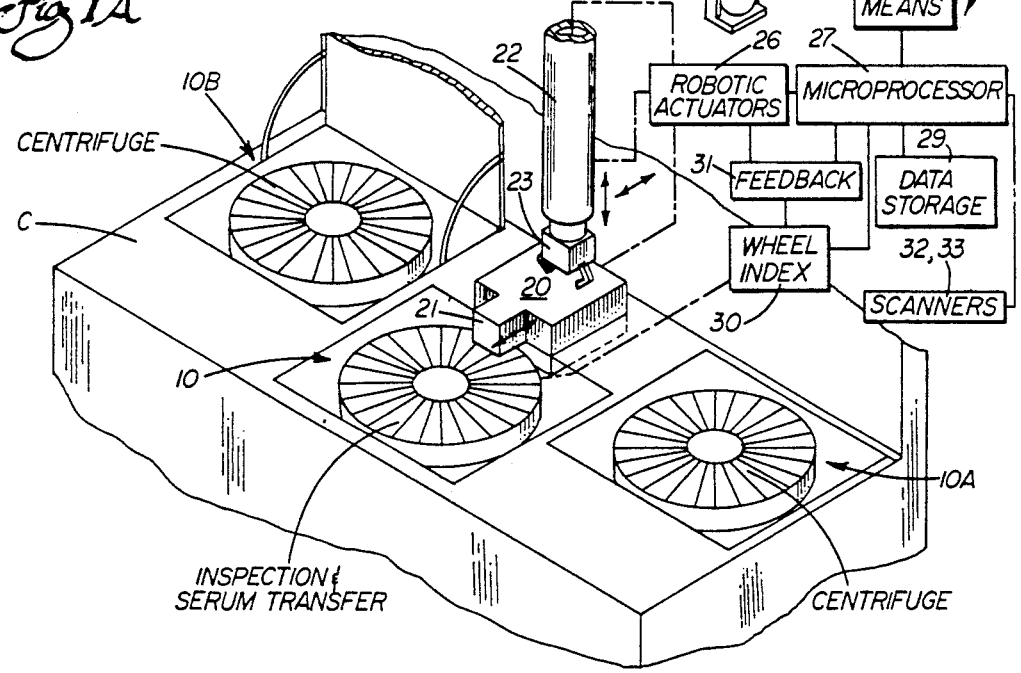
FIG. 1A is a perspective view of a typical console upon which the support wheel of the present invention can be utilized, along with a schematic block diagram of the processing system circuitry of the present invention.

In FIG. 1A, the tube handling wheel 10 of the present invention is illustrated at a center inspection and serum transfer position of a console C. Similar handling wheels may be positioned at one or two other locations on the console C, such as the wheels 10a, 10b. As illustrated, the wheels 10a, 10b preferably undergo centrifuging when positioned in these auxiliary positions. Thus, centrifuge operations can proceed concurrently with the inspection and serum transfer at the wheel 10 in the central position. A processing head 20, including a telescoping portion 21, carries the processing and analyzing transducers, which will be described in more detail below. Above the processing head 20 is a robotic arm 22 including a pick-up head assembly 23 that is operative to pick up and transfer the wheel 10 from the centrifuge positions of the wheels 10a, 10b to the central inspection and serum transfer position, and then to other processing or storage locations.

A control circuit 25 is illustrated in FIG. 1A with dashed line illustration of connections to the wheel 10, the processing head 20 with the telescoping portion 21, the robotic arm 22 and the pick-up head 23. Compositely, robotic actuators 26 carry out the necessary movement of these components, as will be clear as the detailed description progresses.

The heart of the control circuit 25 is a microprocessor 27, which may be one of several available commonly used as a component of programmable index controllers available as off-the-shelf items. An input means 28 may be a keyboard or similar device for programming the microprocessor to carry out the sampling operations. Data storage and memory 29 is provided to maintain the information regarding each individual sample tube 12 and sample cups 13, 14, which information carries through the entire process for the blood analysis.

A wheel index means 30 is shown schematically and is connected to step the wheel 10 in accordance with the program of the microprocessor 27. A mechanical drive, such as a Geneva mechanism with a DC motor, or an electrical stepping motor, are good choices for this index means. A feedback 31 may be provided to keep the microprocessor 27 constantly updated as to the position of the wheel 10, as well as the position of each of the robotic actuators 26. A pair of transducers in the form of scanners, such as a wheel position scanner 32 (see FIG. 1) and a serum scanner 33 are provided and are representative of the control and sampling transducers that may be provided to properly operate the control circuit 25. The position scanner 32 can be responsive to a bar code label 34 on one or more of the arms 15, 16 (only one shown in FIG. 1 on arm 16). The label 34 assures that the microprocessor 27 is inputted with the data for the proper sample tube 12 as each sample is taken. Similarly, each sample tube 12 can be provided with its own bar code label 35 or similar indicia in order to maintain the integrity of the sampling system. The scanner 32 may be programmed to constantly confirm and update information in the microprocessor 27 and the data storage and memory unit 29 from the labels 34, 35.

From the detailed description so far, it can be realized that an advantageous result of the present invention lies in being able to rapidly and accurately process a large number of blood samples without human intervention. The tube holding units 11 are positioned around the full periphery of the wheel 10 and the blood samples are first centrifuged (see wheels 10a, 10b). The wheel being portable, is transferred readily from the centrifuge positions to the central processing position under robotic control. Each tube holding unit 10 is then indexed in turn to the sampling station (see FIG. 1A and compare the uppermost position of FIG. 1). The signals generated by the scanners 32, 33 and others are utilized in the computer circuit 25 to provide full analysis and data storage for the sampling process.

Moving now to a more detailed description of the tube handling wheel 10, reference is made to FIG. 2 wherein the arms 15, 16 are depicted in cross-sectional view. The hub 17 is also shown in cross-section with the central drive and positioning aperture 18 also illustrated. Within the aperture 18 is a key 35 designed to receive a slot in the top portion of a drive shaft of a centrifuge means 36 (see FIG. 4A).

As will be clear from viewing FIG. 4A, the centrifuge 36 causes the tube holder 11 to tilt and the tube 12, as well as the cups 13, 14 to assume a substantially horizontal position. An important feature of the present invention is that the wheel can serve as a bulk holder and storage device for the multiple tube holders 11 without having to transfer the holders between the time of centrifuging and the time of sampling.

To make the transfer of the wheel 10, the pick-up head 23 on the robotic arm 22 includes a clamp assembly comprising a pair of clamps 23a, 23b. The pick-up head 23 is adapted for engagement with an annular shoulder 37 to allow firm gripping and transfer of the wheel 10. The hub 17 further includes through bolts 38 and locking pins 39 in order to provide a rugged structure for the action that occurs in the centrifuge means 36.

In the sampling position for inspection and serum transfer, as shown in FIG. 1A, the wheel 10 outline in FIG. 2. A central locating shaft 41 is seated in the aperture 18 during the processing period. The shaft 41 is slotted to also receive the key 35 to facilitate accurate driving by the wheel index 30.

As best shown in FIGS. 1-3, the sample tube 12, as well as the sample cups 13, 14 have caps 12a, 13a, 14a, respectively. These caps seal each of these containers and do not allow escape of any of the blood. As previously described, the tube 12 is a standard tube that has been evacuated and then filled with blood from a patient by forcing of the blood into the tube by ambient pressure. In order to facilitate entry into the cups 13, 14 one or more can be provided with a star slit cap, as shown as the cap 13a.

The tube is inserted into the holding unit 11 by extending it through spaced retainer rings 45, 46, and so as to rest on the lower platform 47. The tube holding unit 11 further comprises a central body 48 having opposed indentations 49 at the top thereof. These indentations are designed to receive opposed fingers of a robotic manipulator (not shown) that can actually load and unload the individual holding units 11.

As best shown in FIG. 3, a recess 50 is positioned in the body 48. On the opposite side of the recess from the tube 12 is a lateral cup receiver 51 for the sample cups 13, 14. Openings 52 in an upper web 53 retain the sample cups in position (see FIG. 3). A middle web 54 is designed to help assure retention of the cups 13, 14 in the receiver 51. The openings 52 may also be slit around their periphery (not shown) to increase the holding force.

A lower web 55 of the retainer 51 is adapted to set flush on the top of the indexible turntable (see FIG. 2). This mounting assures that the tube holding unit 11 is stabilized during the processing within the central station of the console C (see FIG. 1A).

A pendulum support bar 60 serves to pivotally attach the tube holding unit 11 to the arms 15, 16. In the exploded view of FIG. 3, an extension 61 can be seen to mate with the recess 50. The FIG. 4B position illustrates the manner in which the tube holding unit 11 sits down on the support bar 60. A pivot pin 62 just below the extension 61 extends on both sides of the bar 60 and fits in cooperating slots 63 in adjacent support arms 15, 16. A bar magnet 64 also extends across the support bar 60 and cooperating disc magnets 65 with opposite poles exposed to the ends of the bar magnet 64 serve to form a detent to maintain the support bar 60 and the tube holding unit 11 in the upright position (see FIG. 4B). Also included is an over travel pin 66 that cooperates with a recess 67, as illustrated.

The FIG. 4A illustration depicts the tube holding unit 11 in the centrifuge position upon operation of the centrifuge means 36, as briefly described above. Advantageously, the pendulum support bar 60 allows the entire unit including the tube 12 and cups 13, 14 to pivot in unison. During the centrifuging operation, the cells of the blood are forced by strong centrifugal force into the bottom of the tube leaving the top of the tube filled with the lighter serum (see serum S in FIG. 4B).

It will be remembered that the position of the tube holding unit 11 of FIG. 4B is where the wheel 10 is transferred from one of the side centrifuge positions and is seated on the turntable 40 for sampling. In the preferred embodiment, an aspirating needle 70 pierces the cap 12a of the tube 12, and extends down to approximately the middle part of the tube where the dividing line between the serum and cells is located. The objective is to allow withdrawal of approximately 90% of the serum by the needle 70.

Aspirator 71, to which the needle 70 is attached, is within the telescoping portion 21 of the processing head 20. Once the serum S is withdrawn, the robotic actuators 26 controlling the telescoping portion 21 move the aspirator 71 to deposit the serum, as desired, such as in the sample cups 13, 14 (see aspirators 71a and 71b (FIG. 4B)). In this manner, the separated serum is assured of being maintained with the original blood sample tube 12, and the integrity of the processing system is thus maintained.

The processing head 20 is designed to also house the other scanners or transducers, such as the serum scanner 32 (see FIG. 4C, in addition to FIG. 1). The serum S in the tube 12 can be photoscanned for fibrin, that is, protein string, before the serum is aspirated. This scanning operation occurs at the sampling station, or one station upstream, if desired, so long as the microprocessor 27 is programmed to coordinate the data.

The body 48 of the tube holder 11 includes a concave reflective surface 75 (see FIG. 5). During the photoscanning of the serum S, this surface 75 serves an important function of reflecting maximum light to provide the improved signal to the scanner 32. In this way, an accurate reading of the fibrin is assured.

In summary, a sample processing system particularly adapted for blood, but usable with other liquids that may be hazardous, is provided wherein a tube handling wheel 10 serves as a bulk storage device for a plurality of tube holding units 11. The wheel 10 is transferable by a robotic arm 22 so as to be easily positioned between inspection and centrifuge positions (see FIG. 1A). A unique computer control circuit 25 provides all of the functions of the sampling system without the need for human intervention. The liquid may be fully analyzed and corresponding data generated and stored in a manner heretofore not possible. The individual tube holding units allow the tubes 12, as well as sample cups 13, 14 to be centrifuged, as well as sampled without ever becoming detached from each other. A pendulum support bar 60 provides the appropriate pendulum action for the tube holding unit 11 during centrifuging.

The preferred embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

I claim:

1. A sample processing system for liquids comprising:
   support means
   a plurality of sample containers for liquid positioned for access on said support means for positioning one of said containers at a sampling station;
   robotic process means at said station for processing the liquid sample in each container;
   signal generating means for identifying the container at said station and indicating the condition of said liquid; and
   computer means for analyzing and storing data in response to the signals from said signal generating means, said computer means comprising a microprocessor, input means to program the microprocessor for controlling the sampling of the liquid, and data storage means, whereby the liquid may be analyzed and corresponding data generated and stored without human intervention.

2. The sample processing system in accordance with claim 1, wherein said support means comprises:
   a wheel having a plurality of radial support arms;
   a central support hub for positioning the wheel for processing; and
   container holding means removably positioned between adjacent arms for receiving said containers.

3. The sample processing system in accordance with claim 2, wherein said wheel includes a central hub; and an annular shoulder on said hub to allow pick-up of the wheel for transfer.

4. The sample processing system in accordance with claim 3, wherein is provided a pick-up head for engagement with the annular shoulder on said hub;

said pick-up head including clamp means for engagement with the shoulder and retention during transfer;

clamp actuating means for said clamps; and said clamp actuator operating in response to said computer means.

5. The sample processing system in accordance with claim 1, wherein said containers comprise sample tubes; and cap means for sealing said tubes.

6. The sample processing system in accordance with claim 5, wherein is further provided a tube holding unit for each sample tube;

said tube holding unit including a body and retaining means for said tube; and a lateral receiver extending from said body for sample cups.

7. The sample processing system in accordance with claim 6, wherein said lateral cup receiver includes at least two openings to receive and retain said cups in position substantially parallel to said sample tube.

8. The sample processing system in accordance with claim 7, wherein is provided a pendulum support means positioned between said tube and said cups and engaging the body of said tube holding unit;

pivot means for engaging said support means to provide the pendulum action; and detent means for retaining said pendulum support means and said tube holding unit in the upright position.

9. The sample processing system in accordance with claim 8, wherein said body of said tube holding unit includes a recess positioned between said sample tube and said sample cups;

said pendulum support means including a support bar extending in the upright position when held by said detent means;

an extension above said pivot means for receipt in the recess to mount said tube holding unit; and slot means in said support means for receiving the pivot means;

whereby said tube holding unit, sample tube and sample cups may pivot about a horizontal axis for centrifuging.

10. The sample processing system in accordance with claim 9, wherein said support means includes a wheel having radial support arms;

said tube holding unit being positioned between two adjacent arms on said wheel;

the slot for receipt of said pivot means being formed adjacent the outer radius of the arms; and said lateral cup receiver being positioned between the adjacent arms.

11. The sample processing system in accordance with claim 10, wherein said detent means includes a bar magnet positioned on said pendulum support bar; and disc magnets having opposite poles directed toward said bar magnet on adjacent arms;

whereby the magnet force provides an attraction for said support bar when said tube holding unit is in the upright position.

12. The sample processing system in accordance with claim 11, wherein is further provided an over travel pin on said pendulum support bar; and a recess on said support arms for receiving said over travel pin when said pendulum support bar is in the upright position.

13. The sample processing system in accordance with claim 6, wherein said tube holding unit includes a concave reflector behind said tube;

whereby energy transmitted through the tube is reflected back for improved scanning efficiency.

14. The sample processing system in accordance with claim 1, wherein said process means includes a processing head;

aspirating means in said head for entering and removing at least a portion of said liquid from said container.

15. The sample processing system in accordance with claim 14, wherein said containers comprise sample tubes;

cap means for sealing said tubes;

a tube holder unit for each sample tube;

said tube holder including a body and retaining means for said tube;

a laterally extending receiver extending from said body for sample cups;

said aspirating means being operable to enter and deliver a portion of the liquid removed to said sample cups;

whereby a transfer of liquid can be effected without human intervention.

16. The sample processing system in accordance with claim 4, wherein said processing head further includes energy scanning means for analyzing at least a portion of said liquid in said container.

17. The sample processing system in accordance with claim 16, wherein said liquid is blood;

said scanner means viewing the serum portion of said blood after being centrifuged;

said scanner means being operative to photoscan to determine the fibrin in said blood.

18. The sample processing system in accordance with claim 1, wherein said liquid is blood;

said support means comprising a wheel that is operative for providing centrifuging of said blood to separate the serum from the cells;

said containers comprising sample tubes;

a cap means for sealing said tubes;

a tube holder unit for each sample tube;

said tube holder including a body and retaining means for said tube;

a laterally extending receiver extending from said body for sample cups;

said lateral cup receiver includes at least two openings to receive and retain said cups in position substantially parallel to said sample tube;

a pendulum support means positioned between said tube and said cups and engaging the body of said tube holding unit;

pivot means for engaging said support means to provide the pendulum action; and detent means for retaining said pendulum support means and said tube holding unit in the upright position;

said tube holding unit being operative to pivot through approximately 90° for the centrifuge position;

whereby said tubes and the corresponding cups can be maintained together throughout processing operation.

19. The sample processing system in accordance with claim 1, wherein the liquid is blood;
 said process means including serum scanner means for determination of the fibrin in the serum after centrifuging said blood; and
 aspirating means for removing the serum from the container after centrifuging for placement in separate cups for further analysis;
 said scanner means and said aspirating means being controlled by said computer means.
 transferring said serum to other containers for further processing.

20. The method of processing blood including the steps of:
 supporting a plurality of containers for indexed access at a sampling station;
 indexing said containers in turn to said sampling station;
 centrifuging the blood;
 processing the blood sample at said station including scanning of the blood for fibrin;
 analyzing and storing the data from the signals generated at the process station;
 whereby the blood may be anaylzed and corresponding data generated and stored without human intervention.

21. The method of processing sample liquids of claim 20, wherein the processing further includes aspirating the serum from said containers; and
 transferring said serum to other containers for further processing.

22. A support wheel for a sample processing system for liquids comprising
 a central support hum for positioning the wheel for processing,
 a plurality of radial support arms,
 sample tube means removably positioned between adjacent arms and operatively connected thereto when in position for receiving said sample tubes;
 cap means for sealing said tubes, said sample means being movable relative to said adjacent arms when operatively connected thereto;
 a tube holder unit for each sample tube which unit includes a body and retaining means for said sample tube; and
 a laterally extending receiver extending from said body for sample cups, said receiver being positioned between adjacent arms of said wheel.

23. A tube holding unit in combination with a support wheel for a liquid processing system, said unit comprising
 a body;
 retaining laterally extending from said body for sample cups, said lateral cup receiver including at least two openings to receive and retain said cups in position substantially parallel to said sample tube, said body removably mounted to said parallel to said sample tube, said body removably mounted to said support wheel and pivotally movable relative thereto when mounted;
 said body being provided a recess positioned between said sample tube and said sample cups adopted to receive a pendulum support means for said holding unit;
 said lateral cup receiver including a plurality of horizontal webs, the uppermost web including the openings for said sample cups and the lowermost web of said receiver being operative to securely support the tube holding unit on a surface during processing of said liquid.

24. The tube holding unit for a liquid processing system of claim 23, wherein is further provided:
 a concave reflector positioned behind said tube;
 whereby energy transmitted through the tube is reflected back for improved scanning efficiency.

* * * * *

UNITED STATES PATENT AND TRADEMARK OFFICE
CERTIFICATE OF CORRECTION

PATENT NO. : 5,166,889

DATED : Nov. 24, 1992

INVENTOR(S) : William C. Cloyd

It is certified that error appears in the above-identified patent and that said Letters Patent is hereby corrected as shown below:

In column 10, line 31, 4 should be 14.

In column 12, line 17; insert after "retaining"
 --means for retaining a tube;--

In column 12, line 17; starting as a new paragraph insert
 --a receiver-- before "laterally extending".

In column 12, lines 21 and 22; delete
 "said parallel to said sample tube, said body
 removably mounted to"

Signed and Sealed this

Fourteenth Day of December, 1993

*Attest:*

BRUCE LEHMAN

*Attesting Officer*   *Commissioner of Patents and Trademarks*